US006362375B1

(12) United States Patent
Walker

(10) Patent No.: US 6,362,375 B1
(45) Date of Patent: Mar. 26, 2002

(54) PROCESS FOR THE PREPARATION OF ARYL KETONES GENERATING REDUCED AMOUNTS OF TOXIC BYPRODUCTS

(75) Inventor: Martin Walker, Waterville, VT (US)

(73) Assignee: College of the Holy Cross, Worcester, MA (US)

( * ) Notice: Subject to any disclaimer, the term of this patent is extended or adjusted under 35 U.S.C. 154(b) by 0 days.

(21) Appl. No.: 09/454,083

(22) Filed: Dec. 3, 1999

(51) Int. Cl.$^7$ ............................................. C07C 45/46
(52) U.S. Cl. ..................... 568/319; 568/309; 568/322
(58) Field of Search ................ 568/309, 319, 568/322

(56) References Cited

U.S. PATENT DOCUMENTS

| | | | |
|---|---|---|---|
| 4,721,559 A | 1/1988 | Olah | 208/135 |
| 4,894,482 A | 1/1990 | Lindley et al. | 568/319 |
| 4,990,681 A | 2/1991 | Curtis et al. | 568/324 |
| 5,041,616 A | 8/1991 | Sumner, Jr. | 560/144 |
| 5,110,778 A | 5/1992 | Olah | 502/168 |
| 5,581,011 A | 12/1996 | D'Ambra | 560/8 |
| 5,663,412 A | 9/1997 | D'Ambra | 560/51 |

FOREIGN PATENT DOCUMENTS

| | | | |
|---|---|---|---|
| JP | 9-227442 | 2/1997 | |
| JP | 10087549 | 7/1998 | C07C/49/76 |

OTHER PUBLICATIONS

Desmurs, J.R., et al., "Surprising Catalytic Activity of Bismuth (III) Triflate in the Freidel–Crafts Acylation Reaction," *Tetrahedron Lett.*, 38 (51) :8871–8874 (1997).
Hachiya, I., et al., "Hafnium(IV) Trifluoromethanesulfonate, An Efficient Catalyst for the Friedel–Crafts Acylation and Alkylation Reactions," *Bull. Chem. Soc. Jpn.*, 68:2053–2060 (1995).
Kawada, A., et al., "Lanthanide Trifluoromethanesulfonates as Reusable Catalysts: Freidel–Crafts Acylation," *J. Chem. Soc., Chem Commun.*, 1157–1158 (1993).

Kawada, A., et al., "Scandium Trifluoromethanesulfonate. A Novel Catalyst for Freidel–Crafts Acylation," *Synlett*, 7:544–546 (Jul. 1994).
Kobayashi, S., and Iwamoto, S., "Catalytic Friedel–Crafts Acylation of Benzene, Chlorobenzene, and Fluorobenzene Using a Novel Catalyst System, Hafnium Triflate and Trifluoromethanesulfonic Acid," *Tetrahedron Lett.*, 39:4697–4700 (1998).
Kobayashi, S., "Lanthanides in Aqueous–phase Catalysis," In *Aqueous phase Organometallic Catalysis*, Cornils, B., and Herrmann, W.A., eds. (VCH), pp. 519–528 (1998).
Labrouilliere, M., et al., "An Efficient Method for the Preparation of Bismuth (III) Trifluoromethanesulfonate," *Tetrahedron Lett.*, 40:285–286 (1999).
Lewis, R., ed. "*Hawley's Condensed Chemical Dictionary,*" Twelfth Edition, Von Nostrand Reinhold Co., New York, p. 992 (1993).
March, J., "*Advanced Organic Chemistry*," Third Edition, John Wiley & Sons, New York, pp. 565–566 (1985).
Mine, N., et al., "Trichlorolanthanoid ($LnCl_3$)–Catalyzed Friedel–Crafts Alkylation Reactions," *Chemistry Letters*, pp. 357–360 (1986).
Pearson, D.E., and Buehler, C.A., "Friedel–Crafts Acylations with Little or No Catalyst," *Synthesis*, 1:533–542 (1972).
Smyth, T.P., and Corby, B.W., "Toward a Clean Alternative to Friedel–Crafts Acylation," *Org. Proc. Res. Dev.*, 264 (1997).
Yu, L., et al., Aqueous Aza Diels–Alder Reactions Catalyzed by Lanthanide (III) Trifluoromethanesulfonates, *Tetrahedron Lett.*, 37(13) :2169–2172 (1966).

Primary Examiner—Sreeni Padmanabhan
(74) Attorney, Agent, or Firm—Hamilton, Brook, Smith & Reynolds, P.C.

(57) ABSTRACT

An efficient, cost-effective method useful for the production of aryl ketones that minimizes the generation of toxic byproducts is disclosed. The method utilizes a metal triflate salt to catalyze the reaction between the carboxylic acid substrate and the aromatic substrate. The water generated by the reaction is collected and removed during the process.

31 Claims, No Drawings

PROCESS FOR THE PREPARATION OF ARYL KETONES GENERATING REDUCED AMOUNTS OF TOXIC BYPRODUCTS

BACKGROUND OF THE INVENTION

Aromatic or aryl ketones are commonly used both as chemical intermediates and for producing many useful products. Methods to produce these compounds generally involve condensation of a carboxylic acid derivative with an active aromatic compound. The Friedel-Crafts acylation reaction, which introduces an acyl group into an aromatic ring to produce an aryl ketone, is considered the most important method for the formation of aryl ketones and is widely used commercially. In its most common form, the reaction occurs between an acyl halide, generally an acyl chloride, and an aromatic substrate and is catalyzed by aluminum trichloride. The mechanism of the reaction is represented by the following:

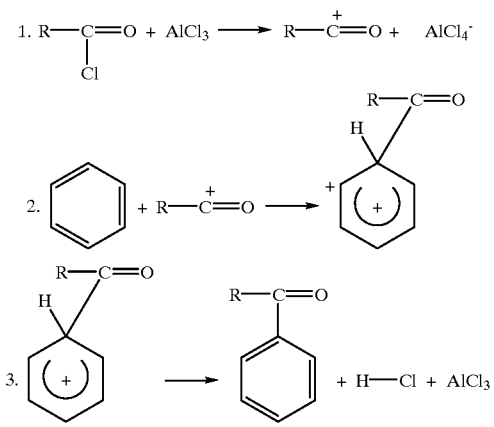

(March, J., "*Advanced Organic Chemistry*", Third Edition, John Wiley & Sons, New York, 1985, 565–566).

Despite its widespread acceptance, this common method has a number of serious disadvantages, including the generation of significant amounts of toxic byproducts which must be disposed of as hazardous waste materials (Desmurs, J. R., et al., 1997, *Tetrahedron Lett* 38:8871–8873). The amount and toxicity of the waste materials produced are a result of the chemical composition of the acyl chloride substrate and the aluminum chloride catalyst, the requirement for a stoichiometric amount of catalyst and the necessity of using a chlorinated hydrocarbon solvent, carbon disulfide or nitrobenzene (Smyth, T. R. et al., 1997, *Org Proc Res Dev* 264). Moreover, the spent catalyst is not readily recoverable for reuse (Kawada, A. et al., 1993, *J Chem Soc, Chem Commun* 1157–1158).

In recent years, much chemical and environmental research has been directed to improving the Friedel-Crafts acylation reaction. For example, attempts have been made to utilize substrates other than acyl halides for Friedel-Crafts acylation reactions. The majority of those methods utilize the readily reactive acyl anhydrides, but it has been recognized that these starting materials require catalyst in even greater amounts than do acyl halides. The additional catalyst is required due to the necessity for converting the acyl compound to the acyl cation (March, J., "*Advanced Organic Chemistry*", Third Edition, John Wiley & Sons, New York, 1985, 565–566, 565). Moreover, such reactions only utilize a single acyl group, wasting the second acyl group.

A few studies have examined the direct use of carboxylic acid substrates. Unfortunately, these methods generally require the use of very strong or protic acids, such as hydrogen fluoride, sulfuric acid or polyphosphoric acid, as the catalyst (Lindley, D., et al., 1990, U.S. Pat. No. 4,894,482; Curtis, T. A. et al., U.S. Pat. No. 4,990,681; Sumner Jr., 1991,U.S. Pat. No. 5,041,616). Thus, the methods not only produce very toxic byproducts, they must be conducted in a highly corrosion-resistant environment.

The use of alternative catalysts has also been considered. For example, metal triflate salts have been used for organic synthesis reactions in general (Labrouillerer, M. et al., 1999, *Tetrahedron Lett* 40:285–286), and Friedel-Crafts acylations in particular (Kawada, A. et al., 1993, *J Chem Soc, Chem Commun* 1157–1158; *J Chem Soc*; Kawada, A. et al., 1994,*Synlett* 7:545–546;Desmurs, J. R., et al., 1997, *Tetrahedron Lett* 38:8871–8873). These studies utilized either acyl halides or anhydrides as substrates; therefore, the deficiencies associated with the use of those starting materials must be considered when evaluating these methods.

Thus, there exists a need for a more efficient and cost-effective method for producing aryl ketones that minimizes the generation of toxic byproducts.

SUMMARY OF THE INVENTION

The present invention is based, at least in part, on the discovery of an efficient, cost-effective method useful for the production of aryl ketones that minimizes the generation of toxic byproducts. The method utilizes a carboxylic acid substrate which eliminates both the necessity for forming the acyl chloride starting material, and the reaction step in which the acid chloride intermediate is formed in the common Friedel-Crafts acylation reaction. The method also utilizes a metal triflate salt catalyst which can be recovered and reused after the reaction is complete. In addition, water, the major byproduct formed by the reaction, is collected and removed during processing.

In one embodiment, a method of preparing an aryl ketone represented by the following structural formula:

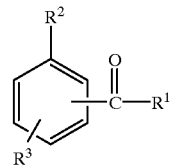

comprising heating an aromatic compound represented by the following structural formula:

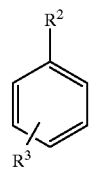

with a carboxylic acid in the presence of (1) a volatile organic compound which forms an azeotrope with water, and (2) a catalytic amount of a metal triflate salt, wherein the water of reaction is removed from the reaction mixture, and wherein:

$R^1$ is the residue of the carboxylic acid;

$R^2$ is an a hydrogen, hydroxy, alkyl, alkoxy, aryl, aryloxy or halogen group;

$R^3$ is a hydrogen, hydroxy, alkyl, alkoxy, aryl, aryloxy or halogen group or any combination thereof; or $R^2$ and $R^3$ collectively are a divalent chain of atoms forming a fused ring with the benzene ring to which each is attached.

In a preferred embodiment, the method is carried out at a temperature of less than about 85, 110, 132 or 140° C.

In a preferred embodiment, the volatile organic compound is an aliphatic or aromatic hydrocarbon. In a preferred embodiment, the volatile organic compound is an aryl halide. In particularly preferred embodiments, the volatile organic compound is toluene.

In a preferred embodiment, the metal triflate catalyst is a rare metal triflate catalyst. In a particularly preferred embodiment, the metal triflate catalyst is a rare earth metal triflate catalyst.

In another embodiment, an improved Friedel-Crafts acylation reaction is provided comprising the steps of generating an acylium ion through the acceptance of an electron pair from a carboxylic acid by a metal triflate catalyst, followed by loss of water in an organic solvent which forms an azeotrope with water; reacting the acylium ion with an aromatic substrate; and removing the water of reaction from the reaction mixture, thereby forming an aryl ketone.

In a preferred embodiment, the reaction is carried out at a temperature of less than about 85, 110, 132 or 140° C.

In a preferred embodiment, the volatile organic solvent is an aliphatic or aromatic hydrocarbon. In a preferred embodiment, the volatile organic compound is an aryl halide. In a particularly preferred embodiment, the volatile organic solvent is toluene.

In a preferred embodiment, the metal triflate catalyst is a rare metal triflate catalyst. In a particularly preferred embodiment, the metal triflate catalyst is a rare earth metal triflate catalyst.

In another embodiment, a method of preparing an aryl ketone represented by the following structural formula:

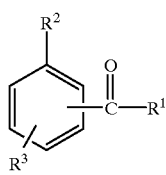

comprising heating an aromatic compound represented by the following structural formula at a temperature less than about 140° C.

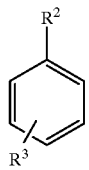

with a carboxylic acid in the presence of (1) toluene, and (2) a catalytic amount of a rare earth metal triflate, wherein the water of reaction is removed from the reaction mixture, and wherein:
$R^1$ is the residue of the carboxylic acid;
$R^2$ is a hydrogen, hydroxy, alkyl alkoxy, aryl, aryloxy or halogen group;
$R^3$ is a hydrogen, hydroxy, alkyl, alkoxy, aryl, aryloxy, halogen group or any combination thereof; or
$R^2$ and $R^3$ collectively are a divalent chain of atoms forming a fused ring with the benzene ring to which each is attached.

DETAILED DESCRIPTION OF THE INVENTION

A description of preferred embodiments of the invention follows. It will be understood that the particular embodiments are shown by way of illustration and not as limitations. The principle features of this invention can be employed in various embodiments without departing from the scope of the invention. All parts and percentages are by weight unless otherwise specified.

A variety of metal triflates can be used as catalysts in the methods of the invention. The language "metal triflate" is intended to include a compound formed from a metal and a trifluoromethanesulfonate. Preferred compounds are salts. The salts can be either anhydrous salts or can contain waters of hydration.

A triflate catalyst can be formed from many metals. Any metal, which when combined with a trifluoromethanesulfonate to form a metal triflate, effectively catalyzes the reactions of the invention can be used. Preferred metal triflates include those in which the metal is a rare metal. The language "rare metal" is intended to include a chemical element of Groups III, IV and V of the periodic table including the transition elements in the lanthanide and actinide series. Preferred rare metal triflates include the rare earth metals as well as indium triflate, hafnium triflate, bismuth triflate and thorium triflate. The language rare metal is intended to encompass the language "rare earth metal" in its art recognized broadest form. Thus, the language rare earth metal is intended to include a chemical element from the group of chemically related elements of Group IIIB of the periodic table, e.g., the lanthanoid series, e.g., the lanthanide series plus the elements scandium and yttrium (Lewis, R., editor, "*Hawley's Condensed Chemical Dictionary*", Twelfth Edition, Von Nostrand Reinhold Company, New York, 1993, 992). Preferred rare earth metal triflate catalysts are those of the lanthanide series. Particularly preferred rare earth metal triflate catalysts include several from the lanthanide series including lanthanum triflate, cerium triflate, praseodymium triflate, neodymium triflate, samarium triflate, dysprosium triflate and ytterbium triflate, as well as scandium triflate and yttrium triflate.

The metal triflate catalysts can be obtained commercially, for example, indium triflate and ytterbium triflate can be purchased from the Strem Chemical Company, Newburyport, Massachusetts. Such catalysts are suitable for direct use in the anyhydrous form supplied.

Alternatively, the catalysts can be prepared from various starting materials. For example, the appropriate metal oxide can be slurried in water, mixed with a stoichiometric amount of trifluoromethanesulfonic acid and refluxed for a suitable period of time. The resulting suspension can then be filtered and dried to obtain the metal triflate.

A metal acetate or nitrate can also be used as a starting material for preparing a metal triflate. These starting materials can be dissolved in water. In some cases, heating is required to fully dissolve the materials. A stoichiometric amount of sodium hydroxide can be added to the solution. The precipitate formed upon the addition of the sodium hydroxide can be filtered and washed with water. This product is the metal hydroxide which can be mixed with trifluoromethanesulfonic acid to form the metal triflate catalyst.

Alternatively, metal triflates can also be prepared using a triphenyl compound as a starting material. For example, bismuth triflate can be prepared from triphenyl bismuth. Triphenyl bismuth can be slurried in methylene chloride, mixed with a stoichiometric amount of triflouromethane-sulfonic acid and stirred for several minutes. The slurry can then be filtered and the product washed with methylene chloride.

In a typical method of the invention, a catalytic amount of a metal triflate is mixed with a carboxylic acid and an aromatic substrate in a volatile organic substrate.

The language "a catalytic amount" is intended to include the quantitative amount of catalyst required to produce a measurable amount of an aryl ketone from the starting materials contained in a reaction mixture.

The language "carboxylic acid" is intended to include one of a wide variety of unsubstituted and substituted aliphatic, cycloaliphatic and aromatic carboxylic acids containing $C_1$–$C_{20}$ carbons. Carboxylic acids are represented by the following structural formula:

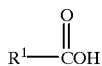

wherein $R^1$ is an unsubstituted or substituted alkyl from $C_1$–$C_8$ carbons, cyclohexyl, phenyl or substituted phenyl. Preferably, $R^1$ is alkyl from $C_1$–$C_{10}$ carbons, phenyl or substituted phenyl.

The language "alkyl" is intended to include a straight chained or branched $C_1$–$C_{110}$ hydrocarbon. The language "lower alkyl" is intended to include a straight chained or branched $C_1$–$C_6$ hydrocarbon or a $C_3$–$C_6$ cyclic hydrocarbon which is completely saturated.

The language "aromatic" is intended to include an activated carbocyclic ring system, e.g., an benzyl and fused polycyclic, carbocyclic ring system, e.g., naphthyl, anthracenyl and 1,2,3,4-tetrahydronaphthyl. In addition, aromatic groups include heteroaryl ring systems, e.g., thiophene, furan, pyrroles, and pyrans, and heteroaryl ring systems in which a carbocyclic aromatic ring, a carbocyclic non-aromatic ring or heteroaryl ring is fused to one or more other heteroaryl rings. For example, benzimidazole, thianaphthene, benzofuran and indole.

The volatile organic solvent can be an aliphatic or an aromatic hydrocarbon, e.g., toluene. The volatile organic solvent can also be an aryl halide. The language "aliphatic" is intended to include a straight chained or branched $C_1$–$C_{18}$ hydrocarbon which is completely saturated or which contains one or more units of unsaturation, or a cyclic $C_3$–$C_{18}$ hydrocarbon which is completely saturated or which contains one or more unconjugated double bonds.

The reaction mixture is refluxed for an appropriate period of time. During the reflux period, the water produced as a byproduct of the reaction as a water-solvent azeotrope is removed from the reaction mixture using any method known to those of skill in the art of organic synthesis. A preferred method utilizes a Dean Stark trap.

The language "azeotrope" is art recognized and intended to include a mixture which forms a constant boiling mixture with water at standard atmospheric pressure.

The resulting solution can then be allowed to cool. The metal triflate catalyst can be recovered from the reaction mixture by aqueous extraction. The organic layers can be washed with, for example, sodium bicarbonate to remove and recover unreacted carboxylic acid. The recovered solid is the aromatic ketone product represented by the following structural formula:

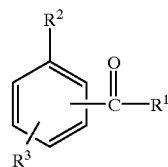

wherein R $R^1$ is the residue of the carboxylic acid;

$R^2$ is a hydrogen, hydroxy, alkyl, alkoxy, aryl, aryloxy or halogen group; and $R^3$ is a hydrogen, hydroxy, alkyl, alkoxy, aryl, aryloxy, halogen group or any combination thereof.

The language "hydroxy" is intended to include an oxygen-hydrogen group, e.g.,- an OH group.

The language "alkoxy" is intended to include an oxygen-alkyl group, e.g., an $OCH_3$ group.

The language "aryl" is intended to include a carbocyclic aromatic ring system and a polycyclic, carbocyclic aromatic ring system.

The language "aryloxy" is intended to include an oxygen-aryl group, e.g., an OpH.

The products formed by the methods of the invention can be analyzed using thin layer chromatography (TLC) using, for example, a 2:1 hexane:ethyl acetate mobile phase. Products can also be assessed using high pressure liquid chromatography (HPLC) using, for example, an Econosil™ (Alltech Associates, Inc., Deerfield, Ill.) C18 column, a 70:30, methanol:$H_2O$ mobile phase, a flow rate of 1.0 ml/min, an ultraviolet wavelength of 254 nm. Nuclear magnetic resonance (NMR), alone or in combination with any of the other analysis systems can be used. In addition, product identity and product purity can be determined by measuring the melting point of the product and comparing it to published melting points.

As evidenced by the products described in the examples, the products formed by the methods of the invention contain an enhanced initial purity. Some products contain a higher initial purity than products formed by the methods of the prior art. Other products contain a lower percentage of contaminants, which are either difficult to remove from the product or whose removal generates toxic byproducts, than do products formed by prior art methods.

In another embodiment, the methods of the invention include an improved Friedel-Craft acylation reaction comprising the steps of generating an acylium ion through the acceptance of an electron pair from a carboxylic acid by a metal triflate catalyst, followed by loss of water in an organic solvent which forms an azeotrope with water; reacting the acylium ion with an aromatic substrate; and removing the water of reaction from the reaction mixture, thereby forming an aryl ketone.

The language "acylium ion" is intended to include the derivative of a substituted oxonium ion or its equivalent. Such ions are generally formed by reacting a substrate with a strong Lewis acid. The acylium ion is a strong electrophile and is represented by the following structural formula:

A typical reaction mechanism of the method is represented by the following:

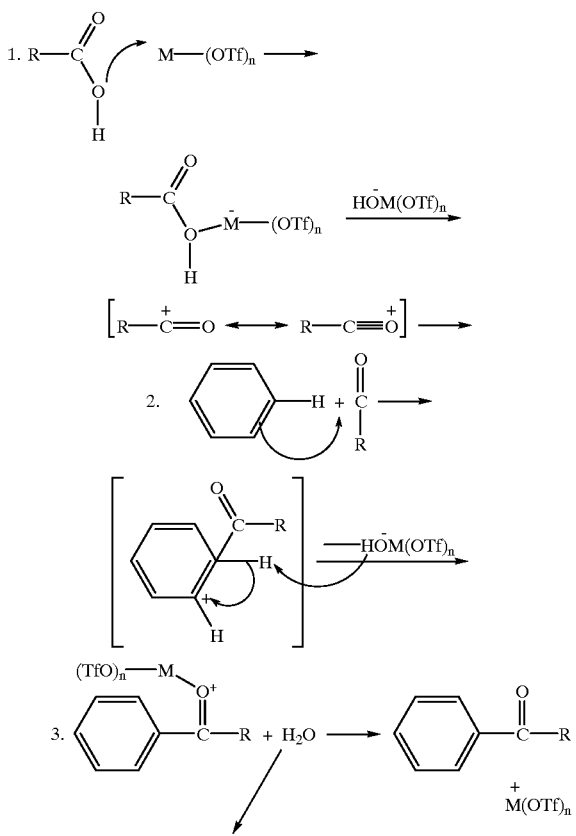

In the reaction depicted above, the highly reactive acylium ion or its equivalent is formed through the acceptance of an electron pair from a carboxylic acid by the metal triflate catalyst, represented by M—(OTf)n, followed by loss of water in an organic solvent. The organic solvent utilized can be toluene or another solvent which forms an azeotrope with water. (In some reactions, the functions of the organic solvent and the aromatic substrate are performed by a single compound, for example, toluene can be used both as the solvent and the aromatic substrate.) The acylium ion is then reacted with an aromatic substrate. Water is collected and removed from the reaction mixture. An aryl ketone containing a group corresponding to the group contained on the carboxylic acid substrate is formed as a product of the reaction.

The methods of the invention provide numerous advantages which enhance the efficient and cost-effective production of aryl ketone products while minimizing the generation of hazardous byproducts. Several of these advantages flow from surprising and unexpected results achieved by the methods.

The methods generally require fewer process steps than the methods of the prior art. This is the result of the direct utilization of the carboxylic acid as the substrate rather than using the more reactive acyl chloride, since doing so obviates the necessity for forming the acyl chloride from the carboxylic acid. Use of the carboxylic acid also eliminates the reaction step in which the acid chloride intermediate is formed in the common Friedel-Crafts acylation reaction.

The methods are also quite flexible in several respects. They can be utilized with a broad range of metal triflate catalysts. This flexibility permits the cost of the catalyst which may fluctuate at different economic times, to be utilized as a factor in the selection of optimal materials and conditions. It is also readily possible to vary the simple reaction conditions, heating until reflux, if necessary to optimize performance of the reaction with any particular catalyst. It has also been discovered that the methods of the invention function quite well even when the metal triflate catalysts are not dry. This permits the use of metal triflate catalyst recovered from a previous reaction to be utilized without even being processed to a dry state. Recovered catalysts can even be added to new reaction mixtures while in solution (see Example 5).

The methods generate very few byproducts, and those generated are either of low toxicity or suitable for reuse, or both. In general, the byproducts produced are water, spent catalyst, residues from a wash to remove excess solvent, e.g., sodium bicarbonate, and distillates from the organic layer after it has been stripped to dryness. The water is removed during the reaction. The catalyst can be recovered for reuse. The residues of the wash are of low toxicity and thus, can be economically discarded or recycled. Similarly, the distillates from the organic layer are of generally low toxicity and, can, in addition, be recovered for reuse as the solvent in future reactions.

Moreover, it has been discovered that the products produced by the methods of the invention are of an enhanced purity. This description of enhanced purity does not mean that the products as initially produced by the methods of the invention necessarily contain a lower percentage of contaminants than similar products produced by methods of the prior art, although they may. Rather, it is intended to convey that the products generally contain fewer contaminants which are either difficult to remove or which generate toxic byproducts when removed.

The contents of all the patents, patent applications and other references cited are hereby expressly incorporated by reference in their entireties.

The invention is further illustrated by the following non-limiting examples.

EXEMPLIFICATION

EXAMPLE 1

Preparation of a Thorium (IV) Triflate Catalyst

Thorium (IV) nitrate (4.81 g) was dissolved in water (15 mL), then a solution of NaOH (1.6 g) in water (10 mL) was added slowly, giving a thick white precipitate. The solid was filtered off, washed with water, then suspended in fresh water (15 mL). A mixture of trifluoromethanesulfonic acid (6.15 g) and water (6 mL) was then slowly added to the suspension, to give a clear, colorless solution. This was stripped in vacuo to give 8.8 g thorium (IV) trifluoromethanesulfonate hydrate, as a damp white solid suitable for use as a catalyst.

ADDITIONAL EXAMPLES RELATED TO EXAMPLE 1

Preparation of Several Metal Triflate Catalysts

Dysprosium (III) trifluoromethanesulfonate hydrate (from the acetate), praesodymium (III) trifluoromethanesulfonate hydrate (from the acetate) and cerium (III) trifluoromethanesulfonate hydrate (from the chloride) were prepared in a similar manner. In the case of the cerium (III) triflate, the final solution was filtered to remove trace amounts of cerium (IV) oxide formed by aerial oxidation of the intermediate hydroxide.

EXAMPLE 2

Preparation of a Lanthanum (III) Triflate Catalyst

Lanthanum (III) carbonate pentahydrate (2.74) was suspended in water (20 mL), and triflic acid (9.0 g) was added dropwise. Once the exothermic addition was complete, a clear colorless solution remained which yielded lanthanum (III) trifluoromethanesulfonate hydrate (14.3 g, as a glassy wet solid) after water removal in vacuo.

EXAMPLE 3

Preparation of 4,4'-Dimethylbenzophenone with a Praseodymium Triflate Catalyst Praseodymium (III) trifluoromethanesulfonate (3.53 g as a wet solid) and para-toluic acid (1.36 g) were refluxed together in 125 mL toluene with azeotropic removal of the lower water layer (Dean-Stark apparatus). After 24 hours, the mixture was cooled and extracted with 3×25 mL water, then by 2×25 mL saturated sodium bicarbonate solution. The organic layer was dried using anhydrous sodium sulfate, filtered, then concentrated down in vacuo to give crude 4,4'-dimethylbenzophenone (0.65 g, 31% yield) as a cream-colored crystalline solid. This was then recrystallized from methanol to give white needles of pure 4,4' dimethylbenzophenone (0.19 g, 9% yield) (M.P. 90.5–91.5° C.).

ADDITIONAL EXAMPLES RELATED TO EXAMPLE 3

Preparation of 4,4'-Dimethylbenzophenone with Several Metal Triflate Catalysts The procedure described in Example 3 was followed, except that different catalysts were used in place of dysprosium (III) trifluoromethanesulfonate. Yields are yields of pure, recrystallized products, except those in parentheses which are yields assessed at the crude stage using HPLC. The yields were as follows:

| Catalyst | $Sc(OTf)_3$ | $Y(OTf)_3$ | $In(OTf)_3$* | $Dy(OTf)_3$ | $Yb(OTf)_3$* | $Bi(OTf)_3$ | $Th(OTf)_4$ |
|---|---|---|---|---|---|---|---|
| % Yield | 4 | (12) | (17) | (16) | (11) | 5 | (21) |

*Commercial samples of anhydrous catalysts were used.

It was found that indium and bismuth trifluoromethanesulfonates could not be recovered in acceptable yield from the aqueous extracts using the procedure of Example 3. However, some additional study directed to this aspect of the procedure will likely result in increased recovery of these two catalysts.

EXAMPLE 4

Preparation of 4,4'-Dimethylbenzophenone with Cerium Triflate Recovered Catalyst Cerium(III) trifluoromethanesulfonate (3.23 g as a wet solid) and para-toluic acid (1.36 g) were refluxed together in 125 mL toluene as in Example 3, but for 48 hours. After work-up (as in Example 3) crude 4,4'-dimethylbenzophenone (0.64 g, 30% yield) was obtained as a cream-colored crystalline solid.

The three water extracts from above (excluding the $NaHCO_3$ extracts) were combined and stripped down to give a damp solid which was used as the catalyst for a second batch. The procedure used was exactly as for Example 3, except that the reflux was maintained for 100 hours. After workup (as for Example 3), 4,4' dimethylbenzophenone was obtained (1.65 g, 79% yield), which was determined by $^1H$ NMR to be practically pure (M.P. 84.5–86.5° C.).

EXAMPLE 5

Preparation of 4,4'-Dimethylbenzophenone with a Solution of Recovered Catalysts The three water extracts from Example 4 (excluding the $NaHCO_3$ extracts) were charged into a 200 mL flask along with toluene (50 mL) and para-toluic acid (1.36 g). The mixture was heated and water was removed azeotropically as in Example 3; once approximately 40 mL of water had been removed a further 50 mL toluene was added. Then, when a total of 75 mL of water had been removed, a final 25 mL toluene was added. The reflux was terminated after 18 hours. After workup (as in Example 3) the reaction gave crude 4,4'-dimethylbenzophenone (0.58 g, 28% yield), which was again practically pure by $^1H$ NMR (M.P. 86.5–87.5° C.). Removal of water from the three water extracts recovered 3.40 g cerium (III) trifluoromethanesulfonate as a damp, off-white solid).

EXAMPLE 6

Preparation of 4-Methoxy-4'-methylbenzophenone with a Praseodymium Triflate Catalyst Praseodymium (III) trifluoromethanesulfonate (1.18 g as a wet solid), trifluoromethanesulfonic acid (0.30 g), anisole (2.38 g) and para-toluic acid (2.72 g) were refluxed together in 175 mL toluene with azeotropic removal of the lower water layer (Dean-Stark apparatus). After 22 hours, the mixture was cooled and extracted with 3×25 mL water, then by 2×25 mL saturated sodium bicarbonate solution. The organic layer was dried using anhydrous sodium sulfate, filtered, then concentrated down in vacuo to give crude 4-methoxy-4'-methylbenzophenone (2.7 g, 60% yield) as a cream-colored crystalline solid.

EXAMPLE 7

Preparation Of Para-methoxy-2-ethylbutyrophenone with a Dysprosium Triflate Catalyst Dysprosium (III) trifluoromethanesulfonate (3.66 g as a wet solid), anisole (1.08 g) and 2-ethylbutanoic acid (1.16 g) were refluxed together in 125 mL toluene with azeotropic removal of the lower water layer (Dean-Stark apparatus). After 48 hours, the mixture was cooled and extracted with 3×25 mL water, then by 2×25 mL saturated sodium bicarbonate solution. The organic layer was dried using anhydrous sodium sulfate, filtered, then concentrated down in vacuo to give para-methoxy-2-ethylbutyrophenone (0.90 g, 44% yield) as an amber-colored oil, which was practically pure by $^1H$ NMR analysis. Removal of water from the three water extracts recovered 3.54 g as a damp, off-white solid.

ADDITIONAL EXAMPLES RELATED TO EXAMPLE 7

Preparation of Additional Aryl Ketones with a Dysprosium Triflate Catalyst

In like manner to Example 7, anisole and para-toluic acid were reacted together (90 hour reflux) to give crude 4-methoxy-4'-methylbenzophenone (1.84 g, 81% yield) as a cream-colored crystalline solid. This was recrystallized from methanol to give the ketone as pure ($^1$H NMR) white needles, M.P. 81.5–83.50 C. (0.87 g, 30% yield). Removal of water from the three water extracts recovered 3.86 g catalyst as a damp, off-white solid.

In like manner to Example 7, anisole and para-toluic acid were reacted together (24 hour reflux) to give crude 4,4'-dimethoxybenzophenone (0.85 g, 35% yield). This was recrystallized from methanol to give the ketone as pure ($^1$H NMR) glistening white flakes, M.P. 138–139° C. (0.40g, 16% yield). Removal of water from the three water extracts recovered 3.39 g catalyst as a damp, off-white solid.

EXAMPLE 8

Preparation of 4-Methoxy-4'-methylbenzophenone with a Hafnium Triflate Catalyst Hafnium (IV) trifluoromethanesulfonate (5.15 g), anisole (1.08 g) and para-toluic acid (1.36 g) were refluxed together in 125 mL chlorobenzene with azeotropic removal of the upper water layer (inverse Dean-Stark apparatus). After 3 hours, the mixture was cooled and extracted with 2×25 mL water, then 2×25 mL saturated sodium bicarbonate solution. The organic layer was dried using anhydrous sodium sulfate, filtered, then concentrated down in vacuo to give crude 4-methoxy-4'-methylbenzophenone (0.20 g, 9% yield) as a colored crystalline solid. The aqueous layer was concentrated in vacuo to give 4.41 g of a damp, white solid.

ADDITIONAL EXAMPLES RELATED TO EXAMPLE 8

Preparation of 4-Methoxy-4'-methylbenzophenone with a Hafnium Triflate Catalyst with Recrystallization In like manner to Example 8, anisole and para-toluic acid were reacted together (4 hour reflux) in chlorobenzene in the presence of ytterbium (III) trifluoromethanesulfonate hydrate, to give crude 4-methoxy-4'-methylbenzophenone (0.15 g, 7% yield).

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing an aryl ketone represented by the following structural formula:

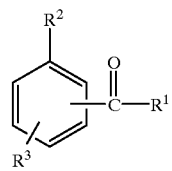

comprising heating an aromatic compound represented by the following structural formula:

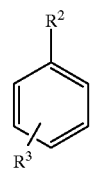

with a carboxylic acid in the presence of (1) a volatile organic compound which forms an azeotrope with water, and (2) a catalytic amount of a metal triflate, wherein the water of reaction is removed from the reaction mixture, and wherein:

$R^1$ is the residue of the carboxylic acid;

$R^2$ is a hydrogen, hydroxy, alkyl, alkoxy, aryl, aryloxy or halogen group;

$R^3$ is a hydrogen, hydroxy, alkyl, alkoxy, aryl, aryloxy, halogen group or any combination thereof; or $R^2$ and $R^3$ collectively are a divalent chain of atoms forming a fused ring with the benzene ring to which each is attached.

2. The method of claim 1, wherein the method is carried out at a temperature of less than about 140° C.

3. The method of claim 1, wherein the volatile organic compound is selected from the group consisting of aliphatic and aromatic hydrocarbons.

4. The method of claim 3, wherein the compound is toluene.

5. The method of claim 1, wherein the metal triflate is a rare metal triflate.

6. The method of claim 5, wherein the rare metal triflate is a rare earth metal triflate.

7. A Friedel-Crafts acylation reaction comprising the steps of:

a) generating an acylium ion through the acceptance of an electron pair from a carboxylic acid by a metal triflate catalyst, followed by loss of water in an organic solvent which forms an azeotrope with water;

b) reacting the acylium ion with an aromatic substrate; and c) removing the water of reaction from the reaction mixture, thereby forming an aryl ketone.

8. The method of claim 7, wherein the method is carried out at a temperature of less than about 140° C.

9. The method of claim 7, wherein the volatile organic solvent is selected from the group consisting of aliphatic and aromatic hydrocarbons.

10. The method of claim 9, wherein the solvent is toluene.

11. The method of claim 7, wherein the metal triflate is a rare metal triflate.

12. The method of claim 11, wherein the rare metal triflate is a rare earth metal triflate.

13. A method of preparing an aryl ketone represented by the following structural formula:

comprising heating an aromatic compound at a temperature less than about 140° C. represented by the following structural formula:

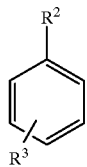

with a carboxylic acid in the presence of (1) toluene, and (2) a catalytic amount of a rare earth metal triflate, wherein the water of reaction is removed from the reaction mixture, wherein:
$R^1$ is the residue of the carboxylic acid;
$R^2$ is a hydrogen, hydroxy, alky, alkoxy, aryl, aryloxy or halogen group;
$R^3$ is a hydrogen, hydroxy, alkyl, alkoxy, aryl, aryloxy halogen group or any combination thereof; or
$R^2$ and $R^3$ collectively are a divalent chain of atoms forming a fused ring with the benzene ring to which each is attached.

14. The method of claim 1, wherein the metal triflate is a hydrate.

15. The method of claim 1, wherein the metal triflate has been recovered from a previous reaction.

16. The method of claim 15, wherein the metal triflate is a wet solid when added to the reaction mixture.

17. The method of claim 15, wherein the metal triflate is in a solution when added to the reaction mixture.

18. The method of claim 7, wherein the metal triflate catalyst is a hydrate.

19. The method of claim 7, wherein the metal triflate catalyst has been recovered from a previous reaction.

20. The method of claim 19, wherein the metal triflate catalyst is a wet solid when added to the reaction mixture.

21. The method of claim 19, wherein the metal triflate catalyst is in a solution when added to the reaction mixture.

22. A method of preparing an aryl ketone represented by the following structural formula:

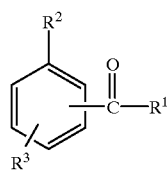

comprising heating an aromatic compound represented by the following structural formula:

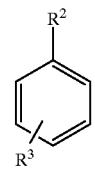

with a carboxylic acid in the presence of (1) a volatile organic compound which forms an azeotrope with water, and (2) a catalytic amount of a metal triflate added to the reaction mixture as a wet solid, wherein the water of reaction is removed from the reaction mixture, and wherein:
$R^1$ is the residue of the carboxylic acid;
$R^2$ is a hydrogen, hydroxy, alkyl, alkoxy, aryl, aryloxy or halogen group;
$R^3$ is a hydrogen, hydroxy, alkyl, alkoxy, aryl, aryloxy, halogen group or any combination thereof; or
$R^2$ and $R^3$ collectively are a divalent chain of atoms forming a fused ring with the benzene ring to which each is attached.

23. The method of claim 22, wherein the metal triflate is a hydrate.

24. The method of claim 22, wherein the metal triflate is a rare metal triflate.

25. The method of claim 24, wherein the rare metal triflate is a rare earth metal triflate.

26. The method of claim 22, wherein the metal triflate is in a solution when added to the reaction mixture.

27. A Friedel-Crafts acylation reaction comprising the steps of:
a) generating an acylium ion through the acceptance of an electron pair from a carboxylic acid by a metal triflate catalyst, wherein the metal triflate catalyst is a wet solid when added to the reaction mixture, followed by loss of water in an organic solvent which forms an azeotrope with water;
b) reacting the acylium ion with an aromatic substrate; and removing the water of reaction from the reaction mixture, thereby forming an aryl ketone.

28. The method of claim 27, wherein the metal triflate is a hydrate.

29. The method of claim 27, wherein the metal triflate is a rare metal triflate.

30. The method of claim 29, wherein the rare metal triflate is a rare earth metal triflate.

31. The method of claim 27, wherein the metal triflate catalyst is in a solution when added to the reaction mixture.

* * * * *